(12) United States Patent
Benedetti et al.

(10) Patent No.: US 6,509,322 B2
(45) Date of Patent: *Jan. 21, 2003

(54) PHARMACEUTICAL COMPOSITIONS FOR TOPICAL USE CONTAINING HYALURONIC ACID AND ITS DERIVATIVES

(75) Inventors: Luca Benedetti, Vicenza (IT); Lanfranco Callegaro, Thiene (IT)

(73) Assignee: Fidia Advanced Biopolymers S.R.L., Padua (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 60 days.

(21) Appl. No.: 09/290,873

(22) Filed: Apr. 14, 1999

(65) Prior Publication Data

US 2002/0132790 A1 Sep. 19, 2002

Related U.S. Application Data

(62) Division of application No. 08/591,673, filed as application No. PCT/EP94/02536 on Jul. 29, 1994, now abandoned.

(30) Foreign Application Priority Data

Jul. 30, 1993 (IT) .......................... PD93A0165

(51) Int. Cl.[7] .............................................. A61K 31/70
(52) U.S. Cl. ........................... 514/54; 536/53; 536/114; 536/115; 536/123.1
(58) Field of Search ............................. 514/54; 536/53, 536/114, 115, 123.1

(56) References Cited

U.S. PATENT DOCUMENTS 4,851,521 A 7/1989 della Valle et al. ........ 536/55.1
4,965,353 A 10/1990 della Valle et al. ........ 536/55.1

FOREIGN PATENT DOCUMENTS

| EP | 0138572 | 4/1985 |
| EP | 0341745 | 11/1989 |
| EP | 0518710 | 12/1992 |
| JP | 02101010 | 4/1990 |
| WO | WO9403499 | 2/1994 |

*Primary Examiner*—James O. Wilson
(74) *Attorney, Agent, or Firm*—Birch, Stewart, Kolasch & Birch, LLP

(57) ABSTRACT

The present invention is drawn to a pharmaceutical composition, comprising a pharmaceutically effective amount of an acidic polysaccharide and/or a derivative thereof, a gaseous vehicle, and a pharmaceutically acceptable carrier or excipient. Said acidic polysaccharide or derivative thereof can be hyaluronic acid, a pharmaceutically acceptable salt of hyaluronic acid, a partial or total ester of hyaluronic acid with an alcohol, a partial or total intermolecular ester of hyaluronic acid, a partial or total intramolecular ester of hyaluronic acid, a cross-linked ester of hyaluronic acid, an alginic acid ester, an ester of carboxymethylcellulose, an ester of carboxymethylchitin, an ester of carboxymethyl starch, a gellan ester, a cross-linked gellan ester, a pectic acid ester, and a pectinic acid ester. The composition can contain one or more topical drugs, and can be in the form of an aerosol or liquid spray, a foam, or a dry spray. The composition is useful in the treatment of a variety of pathological situations requiring the acceleration of tissue repair, for example in the treatment of burns, sores, ulcerations, and wounds. Also provided is a therapeutic method, comprising topically administering a pharmaceutical composition comprising a pharmaceutically effective amount of an acidic polysaccharide and/or a derivative thereof in association with a gaseous vehicle and a pharmacologically acceptable excipient, and optionally, one or more topical drugs.

15 Claims, No Drawings

PHARMACEUTICAL COMPOSITIONS FOR TOPICAL USE CONTAINING HYALURONIC ACID AND ITS DERIVATIVES

This application is a divisional of application Ser. No. 08/591,673, filed on Apr. 17, 1996 now abandoned. Application Ser. No. 08/591,673 is the national phase of PCT International Application No. PCT/EP94/02536 filed on Jul. 29, 1994 under 35 U.S.C. §371. The entire contents of each of the above-identified applications are hereby incorporated by reference.

BACKGROUND OF THE INVENTION

1. Field of the Invention

The present invention relates to new pharmaceutical compositions for the topical administration of hyaluronic acid and its derivatives, as well as other acidic polysaccharides and their derivatives. Such compositions can also contain topical drugs. These compositions are produced by combining gaseous vehicles, excipients, etc., compatible with humans and animals, with active principles, thereby facilitating the homogeneous distribution of the hyaluronic acid, hyaluronic acid derivatives, etc., and topical drugs over the skin for the treatment of burns, ulcerations, sores, wounds, etc.

2. Description of Related Art

Acidic polysaccharides represent an important category of natural polymers commonly used in the preparation of pharmaceutical formulations. Of these, hyaluronic acid, a polysaccharide widely found in animals, comprises alternating units of D-glucuronic acid and N-acetyl-D-glucosamine. It is a linear polymer with a wide range of molecular weights which varies according to the source from which it is extracted and the method of purification. In nature, it is present, for example, in pericellular gels, in the fundamental substance of connective tissues of vertebrates, where it is one of the main components, in the synovial fluid of joints, in the vitreous humor, in human umbilical cord tissue, and in cockscombs.

Specific fractions of hyaluronic acid are known which can be employed in various applications depending upon their molecular weight, as described in European Patent No. 0 138 572. The fraction known as HYALECTIN, having a molecular weight of between 500,000 and 730,000 Daltons, does not possess inflammatory activity, and can therefore be used to substitute endobulbar fluids and in therapy for joint pathologies by intraarticular injection, while the fraction known as HYALASTINE, having a molecular weight of between 50,000 and 100,000 Daltons, is suitable for therapeutic use by virtue of its activity in stimulating tissue repair.

Esters of hyaluronic acid with alcohols wherein the carboxy groups are partially or completely esterified are also known, as is their use in the pharmaceutical and cosmetic fields, and in the area of biodegradable plastic materials (U.S. Pat. Nos. 4,851,521 and 4,965,353). EP 0 341 745 describes inter- and intramolecular esters of hyaluronic acid, wherein all or part of the carboxy groups are esterified with hydroxy groups of the same and/or different molecules of the acidic polysaccharide, and their use in the pharmaceutical and cosmetic fields, and in the area of biodegradable plastic materials.

Hyaluronic acid plays a fundamental role in tissue repair processes, especially in the first stages of the process of the formation of granulation tissue, by stabilizing the coagulation matrix and controlling its degradation, favoring the recruitment of inflammatory cells, such as polymorphonucleocytes and monocytes, of mesenchymal cells, such as fibroblasts and endothelial cells, and directing the subsequent migration of epithelial cells. For a review, see Goa et al., "Hyaluronic Acid: A Review of Its Pharmacology and Use as a Surgical Aid in Ophthalmology, and Its Therapeutic Potential in Joint Disease and Wound Healing," *Drugs* 47(3):536–566, 1994.

It is known that the application of hyaluronic acid solutions hastens the healing of bedsores, wounds, and burns (Wokalek et al. "Time Course of Wound Healing," *Journal of Biomaterials Applications* 5:337, 1991). The role of hyaluronic acid in the various stages of tissue repair has been described via a theoretical model by Weigel et al., "A model for the role of hyaluronic acid and fibrin in the early events during the inflammatory response and wound healing", *J. Theor. Biol.* 119:219, 1986.

The foregoing facts demonstrate the importance of hyaluronic acid in the pharmaceutical field.

SUMMARY OF THE INVENTION

It is therefore an object of the present invention to provide a pharmaceutical composition, comprising a pharmaceutically effective amount of an acidic polysaccharide and/or a derivative thereof, a gaseous vehicle, and a pharmaceutically acceptable carrier or excipient. Said acidic polysaccharide or derivative thereof can be hyaluronic acid, a pharmaceutically acceptable salt of hyaluronic acid, a partial or total ester of hyaluronic acid with an alcohol, a partial or total intermolecular ester of hyaluronic acid, a partial or total intramolecular ester of hyaluronic acid, a crosslinked ester of hyaluronic acid, an alginic acid ester, an ester of carboxymethylcellulose, an ester of carboxymethylchitin, an ester of carboxymethyl starch, a gellan ester, a crosslinked gellan ester, a pectic acid ester, and a pectinic acid ester. The composition can be in the form of an aerosol or liquid spray, a foam, or a dry spray, and can contain one or more topical drugs.

Another object of the present invention is the use of an acidic polysaccharide or a derivative thereof to produce a pharmaceutical spray composition useful in the treatment of a variety of pathological situations requiring the acceleration of tissue repair, for example in the treatment of burns, sores, ulcerations, and wounds.

Yet another object of the present invention is to provide a therapeutic method, comprising topically administering a pharmaceutical composition comprising a pharmaceutically effective amount of an acidic polysaccharide and/or a derivative thereof in association with a gaseous vehicle and a pharmacologically acceptable excipient. Such composition can optionally contain one or more topical drugs.

Further scope of the applicability of the present invention will become apparent from the detailed description provided below. It should be understood, however, that the detailed description and specific examples, while indicating preferred embodiments, are merely illustrative, since various changes and modifications within the spirit and scope of the invention will become apparent to those skilled in the art from this detailed description.

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein are herein incorporated by reference in their entirety.

Acidic Polysaccharides and Derivatives Useful in the Present Pharmaceutical Compositions A number of different acidic polysaccharides can be employed in the present pharmaceutical formulations. Among the preferred acidic polysaccharides are hyaluronic acid and salts thereof of various molecular weights. The production and properties of representative hyaluronic acid fractions HYALECTIN and HYALASTINE and are described in European Patent No. 0 138 572.

Also useful are the partial and total esters of hyaluronic acid with various alcohols, including alkyl and arylalkylic alcohols, as described in U.S. Pat. Nos. 4,851,521 and 4,965,353, and the inter- and intramolecular esters of hyaluronic described in EP 0 341 745, wherein part or all of the carboxyl groups are esterified with hydroxyl groups of the same and/or different molecules of hyaluronic acid. Crosslinked esters of hyaluronic acid, described in EP 0 265 116 are also contemplated for use in the formulations of the present invention.

Other acidic polysaccharides contemplated for use in the present pharmaceutical compositions include alginic acid esters, described in EP 0 251 905; gellan esters, described in EP 0 518 710; crosslinked gellan esters, described in PCT Publication WO 94/03499; esters of pectic acid and pectinic acid, described in PCT Publication WO 93/14129; and esters of carboxymethyl-cellulose, carboxymethylchitin, and carboxymethyl starch, described in EP 0 342 557.

Topical Drugs Useful in the Present Pharmaceutical Compositions

The present invention includes spray compositions employing the foregoing acidic polysaccharides and derivatives, alone or in combination, and further, the inclusion of topical drugs along therewith. Representative topical drugs useful in the present formulations are described in EP 0 197 718, and include antimycotic, antibiotic, antiviral, antimicrobial, anti-inflammatory, and anaesthetic substances routinely used in the art for topical application.

Gaseous Vehicles and Delivery of Active Ingredients in the Present Spray Compositions Gaseous vehicles which can be used in the present spray formulations include, for example, n-butane, isobutane, nitrogen, and sterile compressed air.

The dose and distribution of active ingredients delivered via the spray compositions of the present invention are controlled by the valve of the spray atomizer employed, which facilitates delivery of the correct amount of active ingredients over the required area, necessitated by the gravity of the condition to be treated. Such atomizers can deliver single or multiple sprays.

Surfactants Useful in the Present Spray Compositions

A number of different nonionic and anionic surfactants, such as polyoxyethylene derivatives of sorbitan esters and bi- and trivalent metal soaps, can be employed either alone or in combination in the spray compositions of the present invention. Upon application, these compositions produce a foam, which can be easily rubbed into wounds.

Among the sorbitan ester class of polyoxyethylene derivatives, polyoxyethylene sorbitan monolaurate (TWEEN 20), polyoxyethylene sorbitan monopalmitate (TWEEN 40), polyoxyethylene sorbitan monostearate (TWEEN 60), and polyoxyethylene sorbitan monooleate (TWEEN 80), can be employed in the present spray compositions.

Among the bi- and trivalent metal soaps, aluminum stearate and zinc stearate can be employed.

For purely illustrative purposes, described below are some examples of formulations according to the present invention.

EXAMPLE 1

Spray Solution For Topical Use

One 50-ml spray atomizer contains the following components:

| | |
|---|---|
| Hyaluronic acid sodium salt | 100 mg |
| Methylparaben | 30 mg |
| Propylparaben | 15 mg |
| NaCl | 450 mg |
| $H_2O$ q.s. | 50 ml |

The solution containing hyaluronic acid and the excipients is filtered through a 0.2 μm filter and placed in the spray atomizer under sterile conditions Nitrogen, filtered through a 0.2 μm filter at a pressure of 7 atmospheres, is added to the atomizer, which is then fitted with a single-dose valve.

EXAMPLE 2

Spray Solution For Topical Use

A 100-ml spray atomizer contains the following components:

| | |
|---|---|
| Hyaluronic acid sodium salt | 200 mg |
| Methylparaben | 60 mg |
| Propylparaben | 20 mg |
| NaCl | 850 mg |
| $H_2O$ q.s. | 100 ml |

The solution containing hyaluronic acid and its excipients is filtered through a 0.2 μm filter and placed into the spray atomizer under sterile conditions. Nitrogen, filtered through a 0.2 μm filter at a pressure of 7 atmospheres, is added to the atomizer, which is fitted with a single-dose valve.

EXAMPLE 3

Spray Solution For Topical Use

A 100-ml spray atomizer contains the following components:

| | |
|---|---|
| Hyaluronic acid inner ester | 200 mg |
| Methylparaben | 60 mg |
| Propylparaben | 20 mg |

-continued

| | |
|---|---|
| NaCl | 850 mg |
| H₂O q.s. | 100 ml |

The solution containing hyaluronic acid wherein 5% of the carboxy groups are in the form of inner esters and the excipients is filtered through a 0.2-$\mu$m filter and placed in the spray atomizer under sterile conditions. Nitrogen, filtered through a 0.2 $\mu$m filter at a pressure of 7 atmospheres, is added to the atomizer, which is then fitted with a single-dose valve.

EXAMPLE 4

Foam For Topical Use

A 50-ml spray atomizer contains the following components:

| | |
|---|---|
| Hyaluronic acid sodium salt | 100 mg |
| Methylparaben | 30 mg |
| Propylparaben | 15 mg |
| NaCl | 450 mg |
| Tween 20 | 1.5 g |
| Isobutane | 2.0 g |
| H₂O q.s. | 50 ml |

The solution containing hyaluronic acid and excipients is filtered through a 0.2-$\mu$m filter and placed in the spray atomizer under sterile conditions. Isobutane, filtered through a 0.2 $\mu$m filter, is added to the atomizer, which is then fitted with a single-dose valve.

EXAMPLE 5

Foam For Topical Use

A 50-ml spray atomizer contains the following components:

| | |
|---|---|
| Hyaluronic acid sodium salt | 100 mg |
| Methylparaben | 30 mg |
| Propylparaben | 15 mg |
| NaCl | 450 mg |
| Tween 20 | 1.5 g |
| Isobutane | 2.0 g |
| H₂O q.s. | 50 ml |

The solution containing hyaluronic acid and excipients is filtered through a 0.2-$\mu$m filter and placed into the spray atomizer under sterile conditions. Isobutane, filtered through a 0.2 $\mu$m filter, is added to the atomizer, which is then fitted with a single-dose valve.

EXAMPLE 6

Foam For Topical Use

A 100-ml spray atomizer contains the following components:

| | |
|---|---|
| Hyaluronic acid sodium salt | 200 mg |
| Methylparaben | 60 mg |
| Propylparaben | 20 mg |
| NaCl | 850 mg |
| Tween 20 | 3.0 g |
| Isobutane | 4.0 g |
| H₂O q.s. | 100 ml |

The solution containing hyaluronic acid and the excipients is filtered through a 0.2 $\mu$m filter and placed in the spray atomizer under sterile conditions. Isobutane, filtered through a 0.2 $\mu$m filter, is added to the atomizer, which is then fitted with a single-dose valve.

EXAMPLE 7

Foam For Topical Use

A 50-ml spray atomizer contains the following components:

| | |
|---|---|
| Hyaluronic acid sodium salt | 100 mg |
| Methylparaben | 30 mg |
| Propylparaben | 15 mg |
| NaCl | 450 mg |
| Aluminum stearate | 1.0 g |
| Isobutane | 2.0 g |
| H₂O q.s. | 50 ml |

The solution containing hyaluronic acid and excipients is filtered through a 0.2 $\mu$m filter and placed in the spray atomizer under sterile conditions. Isobutane, filtered through a 0.2 $\mu$m filter, is added to the atomizer, which is then fitted with a single-dose valve.

EXAMPLE 8

Foam For Topical Use

A 100-ml spray atomizer contains the following components:

| | |
|---|---|
| Hyaluronic acid sodium salt | 200 mg |
| Methylparaben | 60 mg |
| Propylparaben | 20 mg |
| NaCl | 850 mg |
| Zinc stearate | 2.0 g |
| Isobutane | 4.0 g |
| H₂O q.s. | 100 ml |

The solution containing hyaluronic acid and excipients is filtered through a 0.2-$\mu$m filter and placed in the spray atomizer under sterile conditions. Isobutane, filtered through a 0.2 $\mu$m filter, is added to the atomizer, which is then fitted with a single-dose valve.

EXAMPLE 9

Foam For Topical Use

A 100-ml spray atomizer contains the following components:

| | | |
|---|---|---|
| Hyaluronic acid inner ester | 200 mg | |
| Methylparaben | 60 mg | |
| Propylparaben | 20 mg | |
| NaCl | 850 mg | |
| Tween 20 | 3.0 g | |
| Isobutane | 4.0 g | |
| $H_2O$ q.s. | 100 ml | |

The solution containing hyaluronic acid wherein 5% of the carboxy groups are in the form of inner esters and its excipients is filtered through a 0.2 µm filter and placed in the spray atomizer under sterile conditions. Isobutane, filtered through a 0.2 µm filter, is added to the atomizer, which is then fitted with a single-dose valve.

EXAMPLE 10

Dry Spray For Topical Use

A 50 ml spray atomizer contains the following components:

| | |
|---|---|
| Mixture 1 | 2 g |
| N-butane | 35 g |
| Composition of mixture 1 in %: | |
| Hyaluronic acid sodium salt% | 100% |

The hyaluronic acid is micronized in a Retsch ultracentrifugal mill until a fine powder having a mean particle size of 20 µm is obtained. In general, the preferred range for the mean particle size of the powder in the dry sprays of the present invention is from about 0.1 to about 100 µm, more preferably from about 0.1 to about 30 µm. This powder is then placed in the spray atomizer under sterile conditions. Normal-butane, filtered through a 0.2 µm filter, is added to the atomizer, which is then fitted with a single-dose valve.

EXAMPLE 11

Dry Spray For Topical Use

A 50-ml spray atomizer contains the following components:

| | |
|---|---|
| Mixture 2 | 2 g |
| N-butane | 35 g |
| Composition of mixture 2 in %: | |
| Hyaluronic acid sodium salt | 0.2% |
| Alginic acid sodium salt | 99.8% |

The mixture is micronized in a Retsch ultracentrifugal mill until a fine powder having a mean particle size of 15 µm is obtained. This powder is then placed in the spray atomizer under sterile conditions. Normal-butane, filtered through a 0.2 µm filter, is added to the atomizer, which is then fitted with a single-dose valve.

EXAMPLE 12

Dry Spray For Topical Use

A 50-ml spray atomizer contains the following components:

| | |
|---|---|
| Mixture 3 | 2 g |
| N-butane | 35 g |
| Composition of mixture 3 in %: | |
| Hyaluronic acid sodium salt | 0.2% |
| Alginic acid sodium salt | 87.5% |
| $CaCl_2$ | 12.3% |

The mixture is micronized in a Retsch ultracentrifugal mill until a fine powder having a mean particle size of 30 µm is obtained. This powder is then placed in the spray atomizer under sterile conditions. Normal-butane, filtered through a 0.2 µm filter, is added to the atomizer, which is then fitted with a single-dose valve.

EXAMPLE 13

Dry Spray For Topical Use

A 50-ml spray atomizer contains the following components:

| | |
|---|---|
| Mixture 4 | 2 g |
| N-butane | 35 g |
| Composition of mixture 4 in %: | |
| Hyaluronic acid inner ester | 100% |

The hyaluronic acid wherein 5% of the carboxy groups are in the form of inner esters is micronized in a Retsch ultracentrifugal mill until a fine powder having a mean particle size of 20 µm is obtained. This powder is then placed in a spray atomizer under sterile conditions. Normal-butane, filtered through a 0.2 µm filter, is added to the atomizer, which is then fitted with a single-dose valve.

EXAMPLE 14

Dry Spray For Topical Use

A 50-ml spray atomizer contains the following components:

| | |
|---|---|
| Mixture 5 | 2 g |
| N-butane | 35 g |
| Composition of mixture 5 in %: | |
| Hyaluronic acid inner ester | 100% |

The hyaluronic acid wherein 10% of the carboxy groups are in the form of inner esters is micronized in a Retsch ultracentri-fugal mill until a fine powder having a mean particle size of 20 µm is obtained. This powder is then placed in the spray atomizer under sterile conditions. Normal-butane, filtered through a 0.2 µm filter, is added to the atomizer, which is then fitted with a single-dose valve.

EXAMPLE 15

Dry Spray For Topical Use

A 100-ml spray atomizer contains the following components:

| | |
|---|---|
| Mixture 6 | 4 g |
| N-butane | 70 g |
| Composition of mixture 6 in %: | |
| Hyaluronic acid 5% inner ester | 50% |
| Hyaluronic acid 10% inner ester | 50% |

The mixture is micronized in a Retsch ultracentrifugal mill until a fine powder having a mean particle size of 20 μm is obtained. This powder is then placed in the spray atomizer under sterile conditions. Normal-butane, filtered through a 0.2 μm filter, is added to the atomizer, which is then fitted with a single-dose valve.

EXAMPLE 16

Dry Spray For Topical Use

A 100-ml spray atomizer contains the following components:

| | |
|---|---|
| Mixture 7 | 4 g |
| N-butane | 70 g |
| Composition of mixture 7 in %: | |
| Hyaluronic acid 5% inner ester | 0.1% |
| Hyaluronic acid 10% inner ester | 0.1% |
| Alginic acid sodium salt | 87.5% |
| $CaCl_2$ | 12.3% |

The mixture is micronized in a Retsch ultracentrifugal mill until a fine powder having a mean particle size of 20 μm is obtained. This powder is then placed in the spray atomizer under sterile conditions. Normal-butane, filtered through a 0.2 μm filter, is added to the atomizer, which is then fitted with a single-dose valve.

EXAMPLE 17

Dry Spray For Topical Use

| | |
|---|---|
| Mixture 8 | 2 g |
| N-butane | 35 g |
| Composition of mixture 8 in %: | |
| Hyaluronic acid total benzyl ester | 100% |

The hyaluronic acid, totally esterified with benzyl alcohol, is micronized in a Retsch ultracentrifugal mill until a fine powder having a mean particle size of 15 μm is obtained. This powder is then placed in the spray atomizer under sterile conditions. Normal-butane, filtered through a 0.2 μm filter, is added to the atomizer, which is then fitted with a single-dose valve.

EXAMPLE 18

Dry Spray For Topical Use

A 50-ml spray atomizer contains the following components:

| | |
|---|---|
| Mixture 9 | 2 g |
| N-butane | 35 g |
| Composition of mixture 9 in %: | |
| Hyaluronic acid partial benzyl ester | 100% |

The hyaluronic acid, partially esterified with benzyl alcohol, is micronized in a Retsch ultracentrifugal mill until a fine powder having a mean particle size of 15 μm is obtained. This powder is then placed in the spray atomizer under sterile conditions. Normal-butane, filtered through a 0.2 μm filter, is added to the atomizer, which is then fitted with a single-dose valve.

EXAMPLE 19

Dry Spray For Topical Use

A 50-ml spray atomizer contains the following components:

| | |
|---|---|
| Mixture 10 | 2 g |
| N-butane | 35 g |
| Composition of mixture 10 in %: | |
| Hyaluronic acid total ethyl ester | 100% |

The hyaluronic acid, totally esterified with ethyl alcohol, is micronized in a Retsch ultracentrifugal mill until a fine powder having a mean particle size of 15 μm is obtained. This powder is then placed in the spray atomizer under sterile conditions. Normal-butane, filtered through a 0.2 μm filter, is added to the atomizer, which is then fitted with a single-dose valve.

EXAMPLE 20

Dry Spray For Topical Use

A 50-ml spray atomizer contains the following components:

| | |
|---|---|
| Mixture 11 | 4 g |
| N-butane | 70 g |
| Composition of mixture 11 in %: | |
| Hyaluronic acid partial benzyl ester | 0.2% |
| Alginic acid sodium salt | 87.5% |
| $CaCl_2$ | 12.3% |

The mixture is micronized in a Retsch ultracentrifugal mill until a fine powder having a mean particle size of 20 μm is obtained. This powder is then placed in the spray atomizer under sterile conditions. Normal-butane, filtered through a 0.2 μm filter, is added to the atomizer, which is then fitted with a single-dose valve.

EXAMPLE 21

Formulations Containing Topical Drugs

While the foregoing examples describe formulations of the present invention containing various acidic polysaccharide derivatives exemplified by hyaluronic acid and various hyaluronic acid derivatives, also within the scope of the present invention is such formulations further containing various types of topical drugs, alone or in combination with one another.

When the topical drug is an antimycotic substance, for example econazol, this drug can be present in the present formulations in an amount of from about 0.1 to about 1.5% by weight of the total composition.

When the topical drug is an antibiotic substance for example aureomycin, this drug can be present in an amount of from about 0.1 to about 3% by weight of the total composition.

When the topical drug is an antiviral substance, for example acyclovir, this drug can be present in an amount of from about 1 to about 5% by weight of the total composition.

Antimicrobial substances, such as sulfadiazine, can be present in an amount of from about 0.1 to about 2% by weight of the total composition; antiinflammatory substances, such as dexamethasone, can be present in an amount of from about 0.01 to about 0.1% by weight of the total composition; and anaesthetic substances, such as lidocaine, can be present in an amount of from about 0.1 to about 2% by weight of the total composition.

EXAMPLE 22

Pharmaceutical Applications

The pharmaceutical formulations of the present invention can be advantageously used in the medical-surgical field in the treatment of a variety of conditions, such as in the treatment of skin ulcers, sores, wounds, and burns, and in all pathological situations where it is necessary to hasten tissue healing and repair.

The new pharmaceutical formulations for topical administration of hyaluronic acid and other acidic polysaccharides and derivatives thereof can be produced with particular physical characteristics, depending upon the particular polymer and excipients employed. These formulations possess the advantage of associating the polysaccharide with a gaseous vehicle, thus making it possible to uniformly administer and disperse the active principle evenly in the wound, and to modulate the dosage thereof according to the severity of the lesion.

The sprays of the present invention can administer an aerosol, a liquid, a foam, or a cry powder, depending upon the manner of formulation.

Foams, for example, can easily be rubbed into cavity wounds. Sprays consisting of dry, micronized powders also guarantee excellent coverage since the active principle forms a layer of gel which acts as a protective barrier against possible contamination once the powder comes into contact with the wound exudate.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pharmaceutical composition for treating open-wounds, comprising a pharmaceutically effective amount of an active agent selected from the group consisting of hyaluronic acid having a molecular weight of between about 30,000 and about 730,000 Daltons, a partial or total ester of hyaluronic acid with an alcohol, a partial or total intermolecular or intramolecular ester of hyaluronic acid, a gellan ester, and a crosslinked gellan ester;

a gaseous vehicle having a boiling point of $\leq 0°$ C. when measured at ambient pressure; and a pharmaceutically acceptable carrier or excipient for application to an open wound, wherein said composition is in the form of a dry spray or foam.

2. The pharmaceutical composition according to claim 1, wherein said alcohol is an alkyl or arylalkylic alcohol.

3. The pharmaceutical composition according to claim 1, wherein said partial or total ester of hyaluronic acid with an alcohol is hyaluronic acid partially or totally esterified with benzyl alcohol or ethyl alcohol.

4. The pharmaceutical composition according to claim 1, wherein said acidic polysaccharide is a partial or total intermolecular or intramolecular ester of hyaluronic acid.

5. The pharmaceutical composition according to claim 1, wherein said gaseous vehicle is selected from the group consisting of n-butane, isobutane, nitrogen, and sterile compressed air.

6. The pharmaceutical composition according to claim 1, further comprising a surfactant.

7. The pharmaceutical composition according to claim 6, wherein said surfactant is selected from the group consisting of a polyoxyethylene sorbitan ester and a bivalent or trivalent metal soap.

8. The pharmaceutical composition according to claim 7, wherein said polyoxyethylene sorbitan ester is at least one member selected from the group consisting of polyoxyethylene sorbitan monolaurate, TWEEN 20; polyoxyethylene sorbitan monopalmitate, TWEEN 40; polyoxyethylene sorbitan monostearate, TWEEN 60; and polyoxy-ethylene sorbitan monooleate, TWEEN 80.

9. The pharmaceutical composition according to claim 7, wherein said bivalent or trivalent metal soap is at least one member selected from the group consisting of aluminum stearate and zinc stearate.

10. The pharmaceutical composition according to claim 6, which is in the form of a foam.

11. The pharmaceutical composition according to claim 1, further comprising a topical drug.

12. The pharmaceutical composition according to claim 11, wherein said topical drug is at least one member selected from the group consisting of an antimycotic substance, an antibiotic substance, an antiviral substance, an antimicrobial substance, an antiinflammatory substance, and an anaesthetic substance.

13. A method of producing a pharmaceutical dry spray composition of claim 1 comprising combining an acidic polysaccharide or a derivative thereof selected from the group consisting of hyaluronic acid having a molecular weight of between about 30,000 and about 730,000 Daltons, a partial or total ester of hyaluronic acid with an alcohol, a partial or total intermolecular or intramolecular ester of hyaluronic acid, a gellan ester, and a crosslinked gellan ester;

a gaseous vehicle; and a pharmaceutically acceptable carrier or excipient.

14. A method of accelerating tissue repair in an open wound comprising treating a tissue of said open wound in need thereof with an effective amount of the pharmaceutical composition according to claim 1.

15. The method according to claim 14 wherein said tissue comprises a burn, a sore or ulceration or a wound from injury.

* * * * *